United States Patent [19]

Hindley

[11] Patent Number: 4,593,023

[45] Date of Patent: Jun. 3, 1986

[54] 6-OXOMORPHOLINES

[75] Inventor: Richard M. Hindley, Reigate, England

[73] Assignee: Beecham Group p.l.c., England

[21] Appl. No.: 735,357

[22] Filed: May 17, 1985

[30] Foreign Application Priority Data

May 19, 1984 [GB] United Kingdom ............... 8412862

[51] Int. Cl.⁴ ................ A61K 31/535; C07D 265/32
[52] U.S. Cl. ................... 514/233; 514/234; 514/236; 514/237; 514/240; 544/130; 544/141; 544/162; 544/168; 544/169; 544/171; 544/172; 544/173; 544/174; 560/39; 560/42; 562/444
[58] Field of Search ............. 544/130, 141, 162, 168, 544/169, 171, 172, 173, 174; 514/233, 234, 236, 237, 240

[56] References Cited

PUBLICATIONS

Tawaa et al., Chemical Abstracts, vol. 82, (1974), 72896n.

Primary Examiner—Richard L. Raymond
Attorney, Agent, or Firm—Hopgood, Calimafde, Kalil, Blaustein & Judlowe

[57] ABSTRACT

A compound of formula (I):

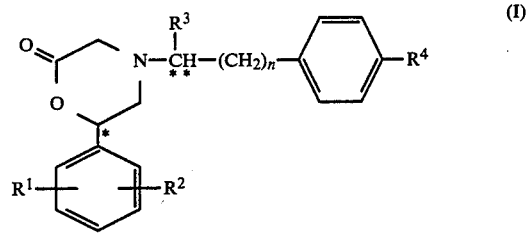

or a pharmaceutically acceptable salt, thereof, in which
$R^1$ is hydrogen, halogen, or trifluoromethyl,
$R^2$ is hydrogen or halogen,
$R^3$ is hydrogen or methyl.
$R^4$ is $-O(CH_2)_a CO_2H$, $-O(CH_2)_b M$, $-CO_2H$ or an ester
or amide derivative thereof in which
a is an integer from 1 to 6,
b is an integer from 2 to 7, and
M is hydroxy, $C_{1-6}$ alkoxy or

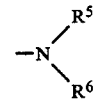

in which
$R^5$ and $R^6$ are each hydrogen or $C_{1-6}$ alkyl or

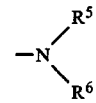

together form a five or six membered ring, and
n is 1 or 2; a process for preparing such a compound and its use in medicine and agriculture.

14 Claims, No Drawings

6-OXOMORPHOLINES

The present invention relates to lactones which have β-agonist activity, to processes for their production and to their use in medicine and agriculture.

According to the present invention there is provided a compound of formula (I):

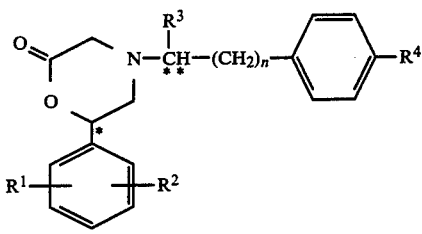

or a pharmaceutically acceptable salt, thereof, in which
$R^1$ is hydrogen, halogen, or trifluoromethyl,
$R^2$ is hydrogen or halogen,
$R^3$ is hydrogen or methyl,
$R^4$ is $-O(CH_2)_aCO_2H$, $-O(CH_2)_bM$, $-CO_2H$ or an ester or amide derivative thereof
in which
a is an integer from 1 to 6,
b is an integer from 2 to 7, and
M is hydroxy, $C_{1-6}$ alkoxy or

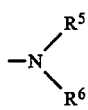

in which
$R^5$ and $R^6$ are each hydrogen or $C_{1-6}$ alkyl
or

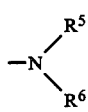

together form a five or six membered ring, and
n is 1 or 2.
Preferably, $R^1$ is in the meta-position.
Preferably a is 1 and b is 2.
Particularly preferred compounds are those wherein $R^3$ is methyl.
Preferably n is 1.

Pharmaceutically acceptable salts of compounds of formula (I) include acid addition salts formed with a pharmaceutically acceptable acid such as hydrochloric acid, hydrobromic acid, orthophosphoric acid, sulphuric acid, methane sulphonic acid, toluenesulphonic acid, acetic acid, propionic acid, lactic acid, citric acid, fumaric acid, malic acid, succinic acid, salicylic acid or acetylsalicylic acid.

Preferred esters of the compounds of formula (I) are $C_{1-6}$ alkyl esters of the compounds wherein $R^4$ is $-CO_2H$ or $-O(CH_2)_aCO_2H$. Particularly preferred esters are methyl and ethyl esters.

Preferred amides of the compounds of formula (I) are those wherein $R^4$ is converted to a group of the formula $-CONR^5R^6$ or $-O(CH_2)_aCONR^5R^6$, where $R^5$ and $R^6$ are as defined in formula (I).

When $R^3$ is methyl, the compounds of formula (I) have two asymmetric carbon atoms, marked with single and double asterisks in the formula. These compounds may, therefore, exist in four stereoisomeric forms. The present invention encompasses all stereoisomers of the compounds of formula (I) whether free from other stereoisomers or admixed with other stereoisomers in any proportion and thus includes, for instance, racemic mixtures of enantiomers.

The absolute configuration of any compound of formula (I) may be determined by conventional X-ray crystallographic techniques.

In a particularly preferred aspect the present invention provides a compound selected from the group consisting of:
4-[2-(2-(3-chlorophenyl)-6-oxomorpholino)propyl]-phenoxyacetic acid methyl ester;
4-[2-(2-phenyl-6-oxomorpholino)propyl]benzoic acid methyl ester; and
N,N-dimethyl-4-[2-(2-(3-chlorophenyl)-6-oxo-morpholino)propyl]phenoxyacetamide; or a pharmaceutically acceptable salt thereof.

The present invention also provides a process for producing a compound of formula (I) or a pharmaceutically acceptable salt, thereof, which comprises cyclising a compound of formula (II) or a salt thereof,

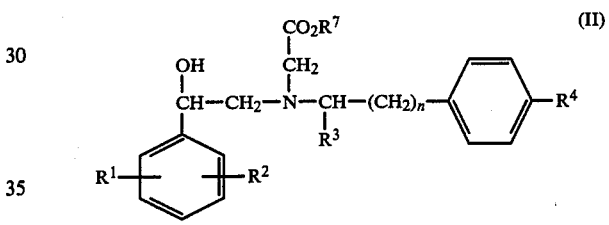

in which $R^1$, $R^2$, $R^3$, $R^4$ and n are as defined in formula (I), and $R^7$ is a $C_{1-6}$ alkyl group or hydrogen, and optionally thereafter converting the compound of formula (I) thus formed to a pharmaceutically acceptable salt, thereof.

The cyclisation process may be carried out under conditions normally used for lactone formation. For example, a compound of formula (II) may be converted to a compound of formula (I) by treatment with hydrogen chloride in diethyl ether at ambient temperature.

The compounds of formula (II) may themselves be prepared by alkylating an amine of formula (III)

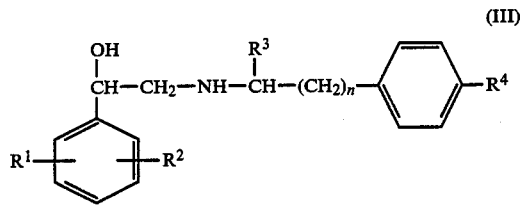

in which $R^1$, $R^2$, $R^3$, $R^4$ and n are as defined in formula (I) with a compound of formula (IV)

$$XCH_2CO_2R^7 \qquad (IV)$$

in which $R^7$ is as defined in formula (II) and X is halogen, preferably bromine.

The alkylation reaction may be carried out in a solvent, preferably butanone, at elevated temperature, preferably under reflux in the presence of potassium carbonate.

Salts of compounds of formula (I) or (II) may be produced by treating a compound of formula (I) or (II) with an appropriate acid, and may be recovered by conventional methods.

Compounds of formula (II) or salts thereof are novel intermediates and as such form a further aspect of the present invention.

Compounds of formulae (III) and (IV) are either known compounds or can be prepared from known compounds by known processes or process analogous to known processes.

Compounds of formula (I) may be separated into diastereoisomeric pairs of enantiomers by, for example, fractional crystallisation from a suitable solvent such as methanol or ethyl acetate or a mixture thereof. The pair of enantiomers thus obtained may be separated into individual stereoisomers by conventional means such as by the use of an optically active acid as a resolving agent.

Suitable optically active acids which may be used as resolving agents are described in *Topics in Stereochemistry'*, *Vol.* 6, Wiley Interscience, 1971, Allinger, N. L. and Eliel, W. L. Eds.

Alternatively any enantiomer of a compound of formula (I) may be obtained by stereospecific synthesis using an optically pure starting material of known configuration.

A compound of formula (I) or a pharmaceutically acceptable salt, thereof (hereinafter 'the drug') may be administered as the pure drug, however, it is preferred that the drug be administered as a pharmaceutical composition also comprising a pharmaceutically acceptable carrier.

Accordingly, the present invention also provides a pharmaceutical composition comprising a compound of formula (I) or a pharmaceutically acceptable salt, thereof with a pharmaceutically acceptable carrier therefor.

As used herein the terms 'pharmaceutical composition' and 'pharmaceutically acceptable' embrace compositions and ingredients for both human and veterinary use.

Usually the compositions of the present invention will be adapted for oral administration although compositions for administration by other routes, such as by injection are also envisaged.

Particularly suitable compositions for oral administration are unit dosage forms such as tablets and capsules. Other fixed unit dosage forms, such as powders presented in sachets, may also be used.

In accordance with conventional pharmaceutical practice the carrier may comprise a diluent, filler, disintegrant, wetting agent, lubricant, colourant, flavourant or the like.

Typical carriers may, therefore, comprise such agents as microcrystalline cellulose, starch, sodium starch glycollate, polyvinylpyrrolidone, polyvinylpolypyrrolidone, magnesium stearate, sodium lauryl sulphate, sucrose and the like.

Most suitably the composition will be provided in unit dose form. such unit doses will normally comprise 0.1 to 1000 mg of the drug, more usually 0.1 to 500 mg and favourably 0.1 to 250 mg.

In a further aspect, the present invention provides a compound of formula (I) for use as an active therapeutic compound.

The present invention further provides a method for treating hyperglycaemia in human or non-human animals which method comprises administering an effective, non-toxic amount of a compound of formula (I) or a pharmaceutically acceptable salt, thereof to a hyperglycaemic human or non-human animal.

The present invention further provides a method for treating obesity in human or non-human animals, which method comprises administering an effective, non-toxic amount of a compound of formula (I) or a pharmaceutically acceptable salt, thereof to an obese human or non-human animal.

Conveniently, the drug may be administered as a pharmaceutical composition as hereinbefore defined, and this forms a particular aspect of the present invention.

In treating hyperglycaemic or obese humans the drug may be taken in doses, such as those described above, one to six times a day in a manner that the total daily dose for a 70 kg adult will generally be about 0.1 to 6000 mg, and more usually about 1 to 1500 mg.

In treating hyperglycaemic or obese animals, especially dogs, the drug may be administered by mouth, usually once or twice a day and at about 0.025 mg/kg to 25 mg/kg, for example 0.1 mg/kg to 20 mg/kg.

In a further aspect the present invention also provides a method for improving the weight gain and/or improving the feed utilisation efficiency and/or increasing lean body mass of livestock, which method comprises the administration to livestock of an effective non-toxic amount of a compound of formula (I) or a veterinarily acceptable salt thereof.

Whilst the compounds of formula (I) and the veterinarily acceptable salts thereof may be administered to any livestock in the abovementioned method, they are particularly suitable for improving the weight gain and/or feed utilisation efficiency and/or lean body mass in poultry, especially turkeys and chickens, cattle, pigs and sheep.

In the preceding method the compounds of formula (I) and veterinarily acceptable salts thereof will normally be administered orally although non-oral modes of administration, for example injection or implantation, are also envisaged. Suitably the compounds are administered in the feed-stuff or drinking water provided for the livestock. Conveniently these are administered in the feed-stuff at from $10^{-3}$ ppm–500 ppm of total daily feed intake, more usually 0.01 ppm to 250 ppm, suitably less than 100 ppm.

The particular formulations used will of course depend upon the mode of administration but will be those used conventionally in the mode of administration chosen.

For administration in feed-stuff the drugs are conveniently formulated as a premix in association with a suitable carrier.

Accordingly, the present invention also provides a veterinarily acceptable premix formulation comprising a compound of formula (I) or a veterinarily acceptable salt thereof in association with a veterinarily acceptable carrier.

Suitable carriers are inert conventional agents such as powdered starch. Other conventional feed-stuff premix carriers may also be employed.

No toxicological effects are indicated when a compound of formula (I) is administered in any of the above mentioned dosage ranges.

The invention will now be illustrated with reference to the following Examples.

In the Examples, the substituents in formula (I) are as shown in the following table:

| Example | $R_1$ | $R_2$ | $R_3$ | n | $R_4$ | Salt |
|---------|-------|-------|-------|---|-------|------|
| 1 | 3-Cl | H | $CH_3$ | 1 | —$OCH_2CO_2CH_3$ | HCl |
| 2 | H | H | $CH_3$ | 1 | —$CO_2CH_3$ | HCl |
| 3 | 3-Cl | H | $CH_3$ | 1 | —$OCH_2CON(CH_3)_2$ | HCl |

EXAMPLE 1

(RR,SS)-4-[2-(2-(3-Chlorophenyl)-6-oxomorpholino)-propyl]phenoxyacetic acid methyl ester hydrochloride Methyl bromoacetate (5 ml) was added to a suspension of (RR,SS)-N-[2-(4-carbomethoxymethoxyphenyl)-1-methylethyl]-2-hydroxy-2-(3-chlorophenyl)ethanamine hydrobromide (2.4 g) and anhydrous potassium carbonate (5 g) in butan-2-one (70 ml). The mixture was boiled under reflux with vigorous stirring for 3 hours. The mixture was cooled and, after filtering, the solvent and excess methyl bromoacetate were removed under vacuum. The residual oil in diethyl ether was treated with ethereal hydrogen chloride to give the title compound, m.p. 191°–195° C., after crystallisation from dichloromethane-diethyl ether.

$^1$H nmr $\delta$(DMSO-$d_6$): 1.15 (3H,d); 2.5–2.85 (1H,d); 3.10–4.10 (10H, complex); 4.75 (2H,s); 6.15 (1H,d); 6.85 (2H,d); 7.15 (2H,d); 7.5 (4H, complex).

EXAMPLE 2

(RR,SS) 4-[2-(2-Phenyl-6-oxomorpholino)propyl]benzoic acid methyl ester hydrochloride The title compound, m.p. 174°–9° C. (dichloromethane-diethyl ether) was prepared from (RR,SS)-N-[2-(4-carbomethoxyphenyl)-1-methylethyl]-2-hydroxy-2-phenylethanamine hemifumarate in a similar manner to that described in Example 1.

$^1$H nmr $\delta$(DMSO-$d_6$): 1.20 (3H,d); 2.8–3.1 (1H, complex); 3.45–4.70 (10H, complex); 6.15 (1H,dd); 7.30–7.65 (7H, complex); 7.8–8.1 (2H,d).

EXAMPLE 3

(RR,SS)-N,N-Dimethyl-4-[2-(2-(3-chlorophenyl)-6-oxo-morpholino)propyl]phenoxyacetamide hydrochloride The title compound, m.p. 204°–208° C. (dichloromethane-ethyl acetate) was prepared from (RR,SS)-N-[2-(4-dimethylaminocarbonylmethoxyphenyl)-1-methylethyl]-2-hydroxy-2-(3-chlorophenyl)ethanamine in a similar manner to that described in Example 1.

$^1$H nmr $\delta$(DMSO-$d_6$+$D_2O$): 1.20 (3H,d), 2.5–4.4 (5H, complex), 2.9 (3H,s), 3.0 (3H,s), 4.30 (2H,s), 4.80 (2H,s), 6.2 (1H,d), 6.85 (2H,d), 7.15 (2H,d), 7.5 (4H, complex).

DEMONSTRATION OF EFFECTIVENESS OF COMPOUNDS

(a) Anti-hyperglycaemic activity

Female CFLP mice, weighing approximately 25 g, were fasted for 24 hours prior to the study. The compounds under study were administered orally as an aqueous solution to each of 6 mice. 30 minutes later a blood sample (10 μl) was obtained from the tail for the analysis of blood glucose. Immediately after taking this blood sample, glucose (1 g/Kg body weight) was administered subcutaneously to each mouse. 6 mice were given water as a control. Blood samples were then obtained from each mouse at 30 minute intervals for 120 minutes.

Compounds that produced a significant (P<0.05) reduction of blood glucose, compared with control mice given water, at any time interval, were considered active. The area under the blood glucose curve over the 2 hour period after the administration of the glucose was calculated for each compound and compared with the value for control animals.

| Example No. | Dose (μmol/Kg) | % Reduction in area under Blood Glucose Curve |
|-------------|----------------|----------------------------------------------|
| 1 | 1 | 50 |
| 2 | 2.5 | 12 |
| 3 | 1 | 52 |

(b) Effect on Energy Expenditure

The effect of the compounds on the energy expenditure of mice was demonstrated by means of the following procedure:

Female CFLP mice, each weighing approximately 24 g were given food and water ad lib before and during the experiment. The compounds were dissolved in water by addition of one mole of hydrochloric acid per mole of compound and these solutions were administered orally to each of 12 mice. A further 12 mice were dosed orally with water. The mice were placed in boxes through which air was drawn and the oxygen content of the air leaving the boxes was measured. The energy expenditure of the mice was calculated for 3 hours after dosing from the volume of air leaving the boxes and its oxygen content, following the principles described by J. B. de V. Weir, *J. Physiol.* (London), 109, 1–9 (1949).

| Example No. | Dose mg/Kg p.o | Mean Energy Expenditure (0–3 h) |
|-------------|----------------|--------------------------------|
| 1 | 22.7 | 156 |
| 2 | 19.5 | 139 |
| 3 | 23.4 | 133 |

I claim:

1. A compound of formula (I):

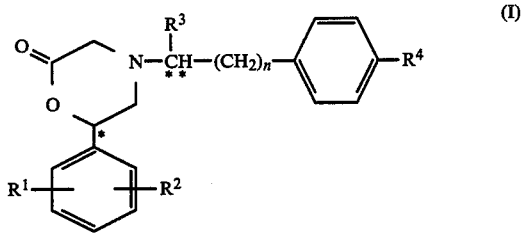

or a pharmaceutically acceptable salt thereof, in which
$R^1$ is hydrogen, halogen, or trifluoromethyl,
$R^2$ is hydrogen or halogen,
$R^3$ is hydrogen or methyl,
$R^4$ is —$O(CH_2)_aCO_2H$, —$O(CH_2)_bM$, —$CO_2H$ or an ester or amide derivative thereof in which
a is an integer from 1 to 6
b is an integer from 2 to 7, and
M is hydroxy, $C_{1-6}$ alkoxy or

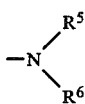

in which
R[5] and R[6] are each hydrogen or $C_{1-6}$ alkyl
or

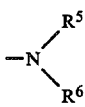

together form a five or six membered ring, and
n is 1 or 2.

2. A compound according to claim 1, wherein R[1] is in the meta-position.

3. A compound according to claim 1, wherein a is 1 or b is 2.

4. A compound according to claim 1, wherein R[3] is methyl.

5. A compound according to claim 1, wherein n is 1.

6. A compound according to claim 1, selected from the group consisting of:
4-[2-(2-(3-chlorophenyl)-6-oxomorpholino)propyl]-phenoxyacetic acid methyl ester;
4-[2-(2-phenyl-6-oxomorpholino)propyl]benzoic acid methyl ester; and
N,N-dimethyl-4-[2-(2-(3-chlorophenyl)-6-oxomorpholino)propyl]phenoxyacetamide; or a pharmaceutically acceptable salt thereof.

7. A compound 4-[2-(2-(3-chlorophenyl)-6-oxomorpholino)propyl]phenoxyacetic acid methyl ester according to claim 1, or a pharmaceutically acceptable salt thereof.

8. A compound 4-[2-(2-phenyl-6-oxomorpholino)propyl]benzoic acid methyl ester according to claim 1, or a pharmaceutically acceptable salt thereof.

9. A compound N,N-dimethyl-4-[2-(2-(3-chlorophenyl)-6-oxomorpholino)propyl]phenoxyacetamide according to claim 1, or a pharmaceutically acceptable salt thereof.

10. A pharmaceutical composition comprising a compound of formula (I) according to claim 1, or a pharmaceutically acceptable salt thereof with a pharmaceutically acceptable carrier therefor.

11. A method for treating obesity in human or non-human animals, which method comprises administering an effective, non-toxic amount of a compound of formula (I) according to claim 1, or a pharmaceutically acceptable salt thereof to an obese human or non-human animal.

12. A method for treating hyperglycaemia in human or non-human animals which method comprises administering an effective, non-toxic amount of a compound of formula (I) according to claim 1, or a pharmaceutically acceptable salt thereof to a hyperglycaemic human or non-human animal.

13. A method of improving the weight gain and/or improving the feed utilisation efficiency and/or increasing lean body mass of livestock, which method comprises the administration to livestock of an effective non-toxic amount of a compound of formula (I) according to claim 1, or a veterinarily acceptable salt thereof.

14. A veterinarily acceptable premix formulation comprising a compound of formula (I) according to claim 1, or a veterinarily acceptable salt thereof in association with a veterinarily acceptable carrier.

* * * * *